United States Patent [19]

Cooper

[11] Patent Number: 5,288,884
[45] Date of Patent: Feb. 22, 1994

[54] PROCESS FOR PRODUCING A REDUCED CALORIE FAT MIMETIC COMPOSITION

[75] Inventor: Charles F. Cooper, Paoli, Pa.

[73] Assignees: Arco Chemical Technology, L.P., Wilmington, Del.; CPC International, Inc., Englewood Cliffs, N.J.

[21] Appl. No.: 964,816

[22] Filed: Oct. 22, 1992

[51] Int. Cl.$^5$ ............................................. C07C 51/00
[52] U.S. Cl. .................... 554/168; 554/164; 554/169; 554/172
[58] Field of Search .............. 554/168, 164, 169, 172, 554/151

[56] References Cited

U.S. PATENT DOCUMENTS

| | | | |
|---|---|---|---|
| 2,610,125 | 9/1952 | Valko | 99/123 |
| 2,625,484 | 1/1953 | Dominick et al. | 99/118 |
| 2,625,485 | 1/1953 | Dominick et al. | 99/118 |
| 2,625,486 | 1/1953 | Nelson et al. | 99/118 |
| 2,625,487 | 1/1953 | Nelson et al. | 99/118 |
| 2,733,251 | 1/1956 | Hawley et al. | 260/410.7 |
| 3,337,595 | 8/1967 | Lamont | 260/410.6 |
| 3,353,964 | 11/1967 | Selden | 99/118 |
| 4,849,242 | 7/1989 | Kershner | 426/601 |
| 4,861,613 | 8/1989 | White et al. | 426/611 |
| 4,895,681 | 1/1990 | Herrmann et al. | 260/410.6 |
| 4,983,329 | 1/1991 | Cooper | 260/410.7 |
| 5,059,443 | 10/1991 | Ennis et al. | 426/531 |
| 5,077,073 | 12/1991 | Ennis et al. | 426/531 |
| 5,118,448 | 6/1992 | Cooper | 554/168 |
| 5,135,683 | 8/1992 | Cooper | 554/151 |
| 5,175,323 | 12/1992 | Cooper | 554/164 |

FOREIGN PATENT DOCUMENTS

| | | |
|---|---|---|
| 353928 | 2/1990 | European Pat. Off. . |
| 396405 | 11/1990 | European Pat. Off. . |
| 396406 | 11/1990 | European Pat. Off. . |
| 433016 | 6/1991 | European Pat. Off. . |
| 481523 | 4/1992 | European Pat. Off. . |
| 481717 | 4/1992 | European Pat. Off. . |
| 1595369 | 4/1970 | Fed. Rep. of Germany . |
| 207070 | 2/1984 | German Democratic Rep. . |
| 5579313 | 3/1991 | Japan . |
| WO91/10368 | 7/1991 | PCT Int'l Appl. . |

OTHER PUBLICATIONS

Aust. et al., *Die Nahrung* 32(1), 49(1988).
Sountag, "Fat Splitting, Esterification, and Interesterification," in *Bailey's Industrial Oil and Fat Products*, vol. 2 4th Ed., Chapter 2, pp. 147–173 (1982).
Sreenivasan, *J. Am. Oil Chem.* 55, 796–805 (1978).
Mieth et al., *Die Nahrung* 27(9), 853(1983).

*Primary Examiner*—Arthur C. Prescott
*Attorney, Agent, or Firm*—Stephen D. Harper

[57] ABSTRACT

A convenient method of obtaining a reduced calorie esterified alkoxylated polyol containing both long chain saturated linear acyl groups and shorter chain unsaturated acyl groups is provided.

20 Claims, No Drawings

PROCESS FOR PRODUCING A REDUCED CALORIE FAT MIMETIC COMPOSITION

FIELD OF THE INVENTION

This invention relates to methods whereby reduced calorie fat substitutes may be conveniently and economically prepared. More specifically, the invention pertains to a synthetic process wherein an esterified alkoxylated polyol which is relatively rich in $C_{20}$–$C_{24}$ saturated linear acyl groups and which is obtained by hydrogenation of a precursor relatively rich in $C_{20}$–$C_{24}$ unsaturated linear acyl groups is reacted with a different esterified alkoxylated polyol composition which is relatively rich in $C_6$–$C_{19}$ unsaturated acyl groups so as to achieve interchange of acyl groups between the two esterified alkoxylated polyols.

BACKGROUND OF THE INVENTION

A wide variety of substances have been proposed for use as fat substitutes in food compositions. The chemical structures of such substances are selected such that they are more resistant to breakdown by the metabolic processes of the human digestive system which normally occur upon ingestion of conventional triglyceride lipids. Because of their increased resistance to digestion and absorption, the number of calories per gram available from the fat substitutes is considerably reduced as compared to common vegetable oils, animal fats, and other lipids. The use of such substances thus enables the preparation of reduced calorie food compositions useful in the control of body weight.

U.S. Pat. No. 4,861,613 (incorporated herein by reference in its entirety) describes one class of particularly useful fat substitutes wherein a polyol such as glycerin is alkoxylated with an epoxide such as propylene oxide and then esterified with any of a number of fatty acids or fatty acid derivatives to form an esterified alkoxylated polyol. These substances have the physical and organoleptic properties of conventional triglyceride lipids, yet are significantly lower in available calories than edible oils owing to their pronounced resistance towards absorption and pancreatic lipase enzymatic hydrolysis. The thermal and oxidative stability of the esterified alkoxylated polyols renders them especially suitable for use in the preparation of reduced calorie food compositions requiring exposure to high temperatures such as fried or baked foods.

Unfortunately, as a consequence of their hydrolytic stability and low digestibility, the esterified alkoxylated polyols described in U.S. Pat. No. 4,861,613 may tend to cause certain undesirable gastrointestinal side effects when consumed at high levels in the diet. That is, since such esterified alkoxylated polyols are not readily broken down into simpler substances upon ingestion, they largely retain their oily, fat-like character and pass through the digestive tract in substantially unaltered form. Non-digestible fat substitutes in general often function as laxatives in much the same manner as mineral oil. Problems with diarrhea, leakage of the fat substitute through the anal sphincter, separation of the fat substitute as an oil from the excreted fecal matter, and shortened bowel transition times resulting in gastrointestinal discomfort can occur as a result of the non-digestibility of the fat substitutes. Other fat substitutes which are similarly resistant towards digestion are known to produce such gastrointestinal side effects. Examples include sucrose polyester which is esterified with up to 8 fatty acid groups; see U.S. Pat. Nos. 3,954,976, 4,005,195, 4,005,196, and 5,006,360. Obviously, such problems will greatly limit the maximum usage level of these substances which can be tolerated in various food compositions, thereby constraining the amount of conventional triglyceride and the number of calories which can be removed from certain foods.

One solution to this problem is provided in copending application Ser. No. 07/886,538, filed May 20, 1992, and entitled "Esterified Propoxylated Glycerin Fat Substitute Compositions Resistant to Gastrointestinal Side Effects" (incorporated herein by reference in its entirety). The copending application describes a fatty acid-esterified propoxylated glycerin composition useful as a reduced calorie fat substitute resistant to gastrointestinal side effects having an average number of oxypropylene units per equivalent of glycerin of from 3 to 20, a fatty acid acyl group content such that at least 40 mole percent of the fatty acid acyl groups in the composition are derived from a $C_{20}$–$C_{24}$ saturated linear fatty acid, and a solid fat index at 27° C. as measured by dilatometry of at least 30. The utilization of such a composition in combination with a conventional fully digestible fatty acid triglyceride fat or oil in a food composition normally containing a fatty component is also described. The copending application suggests that these fatty acid-esterified propoxylated glycerin compositions may be obtained by first propoxylating glycerin with the desired number of equivalents of propylene oxide and then esterifying with a fatty acid or a fatty acid equivalent such as a fatty acid ester, or fatty acid halide, or a fatty acid anhydride.

The use of fatty acid esters in such an esterification step is described in copending application Ser. No. 07/227,048, filed Aug. 1, 1988, now U.S. Pat. No. 5,175,323, entitled "Preparation of Esterified Propoxylated Glycerin by Transesterification" (incorporated herein by reference in its entirety). The fatty acid esters employed in this process are $C_1$ to $C_4$ alkyl esters of saturated or unsaturated $C_{10}$ to $C_{24}$ fatty acids. The esterification reaction is readily driven to completion by removing the $C_1$ to $C_4$ alkyl alcohol generated during the transesterification reaction by distillation or similar means. Although this approach works well on a laboratory scale and affords a high yield of esterified alkoxylated polyol with minimal by-products or color formation, it suffers from the practical disadvantage that the required $C_1$ to $C_4$ alkyl esters are relatively expensive as compared to the corresponding free fatty acids. In addition, great care must be taken to ensure that all of the residual $C_1$–$C_4$ alkyl alcohol formed is removed from the product prior to use in a food composition since certain alcohols of this type (methanol, for example) are considered harmful when ingested.

However, if the $C_{20}$–$C_{24}$ saturated linear acyl groups in the esterified propoxylated glycerin compositions of copending application Ser. No. 07/886,538 are introduced using the corresponding free fatty acids rather than the $C_1$–$C_4$ alkyl esters in order to reduce the overall cost of the esterification, certain other processing problems are encountered. In particular, a direct esterification process must generally be run at a higher temperature than a transesterification process, especially when the only catalytic effect is from the excess fatty acid present. Additionally, a fairly large excess (10–20% molar excess) of fatty acid relative to the initial hydroxyl concentration must be utilized in order to self-catalyze the reaction and to accomplish complete or near-complete esterification of the propoxylated glycerin. As a consequence, the excess fatty acid which remains at the completion of the esterification must be removed prior to formulation of the fat substitute into a food composition, as the excess fatty acid may cause severe taste, odor, and stability problems. A convenient way to remove the excess fatty acid is by vacuum steam stripping the acids away from the esterified propoxylated glycerin composition. This procedure is quite difficult to accomplish when $C_{20}$-$C_{24}$ saturated linear fatty acids are being employed since such acids are relatively high melting (typically, over 74° C.) and consequently readily form troublesome plugs in commercial processing equipment. At times, particularly in vacuum equipment, even steam tracing is not an effective solution due to temperature-lowering effects in the vacuum eductor. As a result, it is often nearly impossible to carry out a large scale non-catalyzed direct esterification of a propoxylated glycerin intermediate with $C_{20}$-$C_{24}$ saturated linear fatty acids without having to frequently shut down to remove plugs of unreacted fatty acid. If a transition metal esterification catalyst such as a zinc, titanium, or tin compound is utilized so as to permit the use of a stoichiometric amount of fatty acid relative to propoxylated glycerin, quantitative removal of the metal catalyst following esterification is often quite difficult to achieve. To be useable as a reduced calorie fat substitutes in food compositions, however, the esterified alkoxylated polyol must be essentially free of such metallic impurities.

Copending application Ser. No. 07/886,538 suggests another method by which the desired $C_{20}$-$C_{24}$ acyl groups may be introduced into an esterified propoxylated glycerin composition. Unsaturated linear fatty acids containing 20 to 24 carbon atoms may be used to esterify a propoxylated glycerin intermediate and the resulting esterified propoxylated glycerin composition may be hydrogenated so as to convert the long chain unsaturated acyl groups to long chain saturated acyl groups. This approach has the advantage of avoiding the use of free fatty acids which are high melting, since $C_{20}$-$C_{24}$ unsaturated fatty acids melt at significantly lower temperatures than their saturated analogues. For example, erucic acid (a $C_{22}$ monounsaturated fatty acid) melts at 33°-35° C. while behenic acid (the corresponding $C_{22}$ saturated fatty acid) melts at 80°-82° C.

However, because the ingestion of lipids containing erucic acid residues has been associated with adverse physiological effects, it will generally be necessary to carry out the subsequent hydrogenation of the esterified propoxylated glycerin under conditions effective to accomplish substantially complete saturation of any acyl groups derived from erucic acid. Such conditions will generally also result in complete hydrogenation of any other monounsaturated acyl groups in the composition as well as at least partial hydrogenation of any di-or polyunsaturated acyl group. It will consequently be difficult to prepare an esterified propoxylated glycerin by this method wherein both $C_{20}$-$C_{24}$ saturated linear acyl groups and $C_6$-$C_{19}$ unsaturated acyl groups are connected via oxyalkylene units to the same glyceryl residue since possible harmful levels of erucic acid residues will likely also be present, thus limiting the usefulness of the composition as a fat substitute in food compositions. It would be highly desirable to develop a method whereby an esterified propoxylated glycerin containing both $C_{20}$-$C_{24}$ saturated linear acyl groups and $C_6$-$C_{19}$ unsaturated acyl groups, but essentially no $C_{22}$ monounsaturated acyl groups derived from erucic acid may be prepared. Such substances may have unique and advantageous properties (solid fat index, hardness, melting point, smoke point, flash point, plasticity, thermal and oxidative stability, etc.) rendering them extremely valuable as fully functional reduced calorie substitutes for conventional triglycerides.

SUMMARY OF THE INVENTION

This invention provides a process for producing a reduced calorie fat mimetic composition comprising the steps of contacting a first esterified alkoxylated polyol characterized by the presence of $C_{20}$-$C_{24}$ unsaturated linear acyl groups with hydrogen in the presence of a transition metal catalyst for a time and at a temperature effective to accomplish hydrogenation of the $C_{20}$-$C_{24}$ unsaturated linear acyl group to yield a second esterified alkoxylated polyol characterized by the presence of at least one $C_{20}$-$C_{24}$ saturated linear acyl group and the absence of $C_{22}$ unsaturated linear acyl groups. The second esterified alkoxylated polyol is contacted with a third esterified alkoxylated polyol characterized by the presence of at least one $C_6$-$C_{19}$ unsaturated acyl group in the presence of a basic catalyst for a time and at a temperature effective to accomplish interchange of the $C_{20}$-$C_{24}$ saturated linear acyl group and the $C_6$-$C_{19}$ unsaturated acyl group to yield the reduced calorie fat mimetic composition.

The incorporation of $C_{20}$-$C_{24}$ saturated linear acyl groups into the final esterified alkoxylated polyol at high levels renders it better tolerated in the digestive tract, as described in the aforementioned copending application. At any level, however, $C_{20}$-$C_{24}$ saturated linear acyl groups have the beneficial effect of increasing the melting or solidification point of an esterified alkoxylated polyol. This increase in melting point may be utilized to help counteract the effect of introducing higher proportions of oxyalkylene groups in an esterified alkoxylated polyol. That is, an increasing degree of propoxylation (moles of propylene oxide reacted per mole of polyol) tends to enhance the non-digestibility and lower the available caloric content of an esterified alkoxylated polyol but also generally depresses the melting point of such a composition. The solid fat index of the substance at a given temperature may consequently be too low for the substance to be directly substitutable for a conventional high-melting triglyceride in a margarine, shortening, cheese, or hard butter (confectionary) application. Increasing the proportion of $C_{20}$-$C_{24}$ saturated linear acyl groups relative to shorter chain, branched, and/or unsaturated acyl groups will favorably affect the melting characteristics of such substances. Another benefit of introducing $C_{20}$-$C_{24}$ linear acyl groups into an esterified alkoxylated polyol is that the caloric availability of the fat mimetic tends to be lower when such groups are present rather than shorter chain acyl groups.

A distinct advantage of the present invention is that it completely avoids the use of free $C_{20}$-$C_{24}$ saturated linear fatty acids in a direct esterification step, thereby minimizing the handling and processing problems which are otherwise encountered. Another advantage is that the relative proportion of shorter chain unsaturated acyl groups in the esterified alkoxylated polyol composition may be varied as desired without introducing possible harmful levels of acyl groups derived from erucic acid.

DETAILED DESCRIPTION OF THE INVENTION

Practice of the process of this invention requires the utilization of a first esterified alkoxylated polyol characterized by the presence of at least one $C_{20}$–$C_{24}$ unsaturated linear acyl group. Preferably, at least one-half of the acyl groups are $C_{20}$–$C_{24}$ unsaturated linear acyl groups. The use of $C_{22}$ monounsaturated linear acyl groups derived from erucic acid (cis-13- docosenoic acid) is especially desirable since erucic acid is readily available from natural sources such as rapeseed oil. The first esterified alkoxylated polyol is additionally characterized by having oxyalkylene units interspersed between attachment sites on a polyol residue (which is typically derived from a polyhydric aliphatic compound) and terminal long chain acyl groups derived from fatty acids. Certain of the acyl groups may be advantageously attached directly to the polyol residue as described in U.S. Pat. Nos. 5,118,448 and 5,135,683 and European Pat. Pub. No. 481,523. The oxyalkylene units favorably influence the caloric availability and/or physical properties of these compositions as compared to triglycerides (natural fats and oils) wherein the polyol (glycerin) residue and all of the acyl groups are directly connected. Illustrative esterified alkoxylated polyols usable in the process of this invention are described, for example, in the following publications, the teachings of which are incorporated herein by reference in their entirety: U.S. Pat. Nos. 4,861,613 (White et al.), 4,983,329 (Cooper), 5,118,448 (Cooper), 5,135,683 (Cooper), 4,849,242 (Kershner), 5,059,443 (Ennis et al.), and 5,077,073 (Ennis et al.); European Pat. Publ. Nos. 481,523 (Sekula), 353,928 (Cooper), and 481,717 (Cooper). Methods for preparing such substances are also well-known and are provided in the foregoing publications.

In an especially preferred embodiment of the invention, the first esterified alkoxylated polyol is comprised of a polyol residue derived from a polyhydric aliphatic compound and from 2 to 8 fatty acid-esterified oxyalkylene groups connected to the polyol residue (through ether linkages). At least one, and preferably at least one-half, of the fatty acid-esterified oxyalkylene groups have the general structure

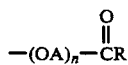

wherein n is from 1 to 20, OA is an oxyalkylene unit derived from a $C_2$–$C_{10}$ epoxide, and

is an acyl group derived from a $C_{20}$–$C_{24}$ unsaturated linear fatty acid.

The polyhydric aliphatic compound may be selected from $C_2$–$C_{10}$ aliphatic diols (e.g., ethylene glycol, propylene glycol, 1,3-propanediol, 1,4-butanediol, 1,2-butanediol, 2,3-butanediol, pinacol, 1,2-cyclohexanediol, 1,2-pentanediol, 1,4-pentanediol, 1,5-pentanediol, 2,4-pentanediol, 3,3-dimethyl-1,2-butanediol, 2-ethyl-2-methyl-1,2-propanediol, 1,2-hexanediol, 1,5-hexanediol, 1,6-hexanediol, 2,5-hexanediol, 2-methyl-2,4-pentanediol, 1,4-cyclohexanediol, 1,7-heptanediol, 2-methyl-2-propyl-1,3-propanediol, 2,2-diethyl-1,3-propanediol, 2,4-dimethyl-2,4-pentanediol, 2-ethyl-1,3-hexanediol, 1,2-octanediol, 1,8-octanediol, 2,2,4-trimethyl-1,2-pentanediol, and the like), $C_3$–$C_{12}$ aliphatic triols (e.g., glycerin, 1,2,4-butanetriol, 2,3,4-pentanetroil, 2-ethyl-2-(hydroxymethyl)-1,3-propanediol, 1,1,1-tris(hydroxymethyl) ethane, 1,2,6-trihydroxyhexane, 1,2,3-heptanetriol, and the like), pentaerythritol, sugar alcohols [including those compounds corresponding to the formula $HOCH_2(CHOH)_nCH_2OH$ wherein n is 2 to 6 such as erythritol, xylitol, sorbitol, arabitol, mannitol, and the like], monosaccharides (e.g., erythrose, threose, ribose, arabinose, xylose, lyxose, allose, altrose, glucose, mannose, gulose, idose, galactose, fructose, galactose, and the like), disaccharides (e.g., sucrose, maltose, lactose) and alkyl glycosides (e.g., methyl glycosides, ethyl glycosides, propyl glycosides, and other glycoside molecules wherein the alkyl glycoside is an acetal formed by interaction of a $C_1$–$C_{20}$ alcohol with a carbonyl group of a mono- or disaccharide such as glucose). Most preferably, the polyhydric aliphatic compound is glycerin (also known as glycerol). The value of n (the number of oxyalkylene units per acyl group) in the first esterified alkoxylated polyol will preferably vary from 1 to 20, but can be manipulated as desired to alter the resistance of the final reduced calorie fat mimetic composition towards digestion and metabolic breakdown as well as the physical properties and characteristics (e.g., melting point, viscosity, relative polarity, solid fat index) of said composition. When the polyhydric aliphatic compound is glycerin, n is preferably 1 to 6. The oxyalkylene units ("OA") are preferably derived by ring-opening $C_2$–$C_{10}$ epoxides, especially aliphatic epoxides, such as ethylene oxide, propylene oxide, 1,2-butylene oxide, (cis and/or trans) 2,3-butylene oxide, isobutylene oxide, 1,2-pentene oxide, cyclohexene oxide, phenyl glycidyl ether, methyl glycidyl ether, ethyl glycidyl ether, styrene oxide, epichlorohydrin, allyl glycidyl ether, and the like. Due to their low cost, high reactivity, and favorable impact on esterified alkoxylated polyol fat substitute properties, the use of ethylene oxide, propylene oxide, 1,2-butylene oxide or mixtures thereof (either in random or block fashion) is especially desirable. Each oxyalkylene unit has the general skeletal formula —C—C—O— containing two carbons and one oxygen. However, the oxyalkylene unit may be substituted with one or more alkyl, aryl, aralkyl, or other such substituent. In a preferred embodiment, the oxyalkylene units correspond to the structure

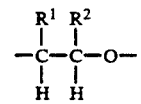

wherein $R^1$ and $R^2$ are the same or different and are hydrogen or a $C_1$–$C_6$ alkyl group such as methyl, ethyl, propyl, isopropyl, butyl, sec-butyl, iso-butyl, tert-butyl, pentyl, hexyl, cyclohexyl, and the like. Most preferably, one of R or $R^1$ is methyl and the other R group is hydrogen. In one desirable embodiment, $R^2$ in the oxyalkylene unit adjacent to the acyl group is a $C_1$–$C_6$ alkyl group since a secondary ester linkage resistant to enzymatic hydrolysis is thereby furnished.

The remaining acyl groups in the first esterified alkoxylated polyol may be nominally derived from a $C_8$–$C_{24}$ saturated or unsaturated fatty acid such as, for example, caprylic acid, capric acid, lauric acid, myristic acid, palmitic acid, palmitoleic acid, stearic acid, oleic acid, elaidic acid, linoleic acid, linolenic acid, arachidic acid, gadoleic acid, behenic acid, lignoceric acid, and the like, subject to the proviso, of course, that at least one of the acyl groups in the first esterified alkoxylated polyol is a $C_{20}$-$C_{24}$ linear unsaturated acyl group (obtained, for example, from fatty acids such as eicosenoic acids, docosenoic acids (including erucic acid), and docosadienoic acids and the like).

The method by which a first esterified alkoxylated polyol having an appropriate acyl group content as described hereinabove is prepared is not critical, but a particularly convenient method is to alkoxylate a polyhydric aliphatic compound such as glycerin with the desired epoxide or mixture of epoxides such as ethylene oxide, propylene oxide, or 1,2-butylene oxide in the presence of a basic catalyst such as a sodium or potassium alkoxide and then esterifying the resulting alkoxylated polyol with a mixture of free fatty acids having a suitable $C_{20}$-$C_{24}$ unsaturated fatty acid content obtained by hydrolytic splitting of a natural triglyceride rich in such $C_{20}$-$C_{24}$ unsaturated fatty acids. For example, many Cruciferous plants produce seeds in which erucic acid (a mono-unsaturated $C_{22}$ fatty acid) is a major or main constituent of the triglycerides found therein.

Illustrative examples of seed fats which can be utilized to provide $C_{20}$-$C_{24}$ unsaturated linear fatty acids useful in the preparation of the first esterified alkoxylated polyol include, but are not limited to, lipids obtainable from plants such as *Brassica alba* (yellow mustard; ca. 7-8 wt. % $C_{20}$ acyl groups and ca. 44-46 wt. % $C_{22}$ acyl groups), *Brassica campestris* (turnip rape, colza; ca. 3-12% $C_{20}$ acyl groups and ca. 40-60 wt. % $C_{22}$ acyl groups), *Brassica juncea* (mustard: ca. 45 wt. % $C_{22}$ acyl groups), *Brassica tournefortii, Sinapis alba* (ca. 51 wt. % erucic acid), *Brassica nigra* (black mustard; ca. 8-9 wt. % $C_{20}$ acyl groups and ca. 43-44 wt. % $C_{22}$ acyl groups), *Brassica napus* (rape), *Cherianthus cheiri* (wallflower; ca. 38-43 wt. % $C_{22}$ acyl groups), *Coringia orientalis* (hare's ear mustard; ca. 10 wt. % $C_{20}$ acyl groups and ca. 35-45 wt. % $C_{22}$ acyl groups), *Erucastrum strigosum* (ca. 48 wt. % $C_{22}$ acyl groups), *Sisymbrium alliaria* (ca. 47 wt. % erucic acid), *Eruca sativa* (jambo rape; ca. 11-12 wt. % $C_{20}$ acyl groups and ca. 37-38 wt. % $C_{22}$ acyl groups), and *Thlaspe arvense* (fanweed; ca. 0-7 wt. % $C_{20}$ acyl groups, ca. 37-49 wt. % $C_{22}$ acyl groups, and ca. 0-4 wt. % $C_{24}$ acyl groups). The seed fats of the Tropaeolum (nasturtium) family also contain high proportions of erucic acid oils. High erucic acid oils from *Crambe abyssinica* and *Crambe hispanica* (ca. 52-57 wt. % 22:1 fatty acid content) could also be used. Another excellent source of $C_{20}$-$C_{24}$ linear unsaturated fatty acids is the oil from the seeds of *Limnathes douglasii* (meadowfoam: ca. 63 wt. % $C_{20}$ acyl groups and ca. 34 wt. % $C_{22}$ acyl groups). Due to its availability and relatively low cost, the mixture of fatty acids derived by hydrolysis of high erucic rapeseed oil is especially preferred for use. The optimum conditions required to accomplish the desired level of esterification and to purify the resulting product will generally be similar to those described in U.S. Pat. No. 4,983,329, incorporated herein by reference in its entirety. Since only minor quantities (generally, from 0 to a maximum of 10 mole % of the total fatty acid mixture) of high melting $C_{20}$-$C_{24}$ saturated linear fatty acids will be present during such a direct esterification step, minimal problems with plugging of overhead lines when vacuum steam stripping such esterification products to remove excess unreacted fatty acid will be encountered.

The first esterified alkoxylated polyol is contacted with hydrogen in the presence of a transition metal catalyst for a time and at a temperature effective to accomplish hydrogenation of the $C_{20}$-$C_{24}$ unsaturated linear acyl groups (minimally, essentially complete conversion of all erucic acid-derived acyl groups to

acyl groups) to yield a second esterified alkoxylated polyol characterized by the presence of $C_{20}$-$C_{24}$ saturated linear acyl groups. If the first esterified alkoxylated polyol contained any shorter chain ($C_6$-$C_{19}$) unsaturated acyl groups, partial or complete hydrogenation of these groups will generally also take place during this step. It is desirable to conduct the hydrogenation under conditions sufficient to lower the $C_{20}$-$C_{24}$ unsaturated linear acyl group content to less than 1 mole %, especially if erucic acid residues are initially present. The second esterified alkoxylated polyol must contain at least one $C_{20}$-$C_{24}$ saturated linear acyl group (more preferably, at least one-half of the acyl groups should be $C_{20}$-$C_{24}$ saturated linear acyl groups).

Surprisingly, it has been discovered that the $C_{20}$-$C_{24}$ unsaturated linear acyl groups may be fully hydrogenated by the process of this invention without degradation or cleavage of the oxyalkylene units or generation of undesirable off-odors or flavors due to by-product formation. The hydrogenation is preferably conducted at a hydrogen pressure of from 0.5 to 20 (more preferably, 0.5 to 10) atmospheres and a temperature of from 75° C. to 275° C. (more preferably, 100° C. to 225° C.), although higher or lower temperatures and pressures may be suitably employed depending upon the reactivities of the particular first esterified alkoxylated polyol and transition metal catalyst utilized. Reaction (contact) times under these conditions of from 0.5 to 24 hours (more preferably, 1 to 12 hours) will normally be effective to achieve a sufficient degree of hydrogenation. Any of the transition metal catalysts known to be useful for the hydrogenation of natural triglycerides may also be utilized to advantage in the instant process, but catalysts wherein the transition metal is platinum, palladium, rhodium, ruthenium, zinc, nickel (e.g., Raney nickel, nickel boride) or copper (especially in the form of copper chromite) are especially preferred for use. Promoters such as chromium, cobalt, thorium, zirconium, titanium, copper and silver, either as such or in the form of oxides or other compounds may also be present. The transition metal catalyst is typically utilized in finely divided form and may advantageously be supported on a porous inert refractory material such as diatomaceous earth, alumina, silica gel, molecular sieves, or kieselguhr or on other types of supports such as carbon (charcoal). Especially preferred for use are "wet-reduced" nickel catalysts containing nickel metal in a matrix of hardened vegetable oil. The catalyst may be heterogeneous (insoluble) or homogeneous (soluble); the heterogeneous catalysts are preferred since they may be readily separated by filtration from the second esterified alkoxylated polyol composition after hydrogenation and reused in subsequent hydrogenations. The optimum amount of catalyst will be dependent upon its activity, the reactivity of the carbon-carbon double bonds in the first esterified alkoxylated polyol, temperature, hydrogen pressure and other factors but will generally be selected such that the concentrations of the transition metal itself is from 100 to 10,000 parts per million. The reaction with hydrogen may be conducted in a batch, continuous or semi-continuous manner in an appropriately configured closed reactor vessel, preferably with good agitation to ensure effective mass transfer of the hydrogen and esterified alkoxylated polyol to and from the surface of the catalyst. Although a solvent may be present, the use of a solvent is not necessary since the first esterified alkoxylated polyol will usually be a free-flowing liquid at the reaction temperatures employed. The hydrogen may be dispersed into the reaction mixture by bubbling or sparging using either a recirculation or dead-end system, for example.

When the desired degree of reaction has taken place, the second esterified polyol thus obtained may be filtered or otherwise treated to remove the transition metal catalyst. For example, nickel removal may be accomplished by a postbleaching step wherein the second esterified alkoxylated polyol after an initial filtration is treated with 0.05–1.0% bleaching earth, activated carbon, or other adsorbent at an elevated temperature (50°–150° C.) and then refiltered. Treatment with acid or ion exchange resins may also be useful. The product thus obtained will be similar in composition to the initial first esterified alkoxylated polyol, with the exception that the product will contain few, if any, $C_{20}$–$C_{24}$ unsaturated linear acyl groups, such groups being essentially entirely replaced by $C_{20}$–$C_{24}$ saturated linear acyl groups.

The second esterified alkoxylated polyol is thereafter contacted with a third esterified alkoxylated polyol characterized by the presence of $C_6$–$C_{19}$ unsaturated acyl groups in the presence of a basic catalyst for a time and at a temperature effective to accomplish interchange of at least one $C_{20}$–$C_{24}$ saturated linear acyl group in the second esterified alkoxylated polyol and at least one $C_6$–$C_{19}$ unsaturated acyl group in the third esterified alkoxylated polyol to produce the desired reduced calorie fat mimetic composition wherein individual esterified alkoxylated polyol molecules bear both $C_{20}$–$C_{24}$ saturated linear groups and $C_6$–$C_{19}$ unsaturated acyl groups.

It will typically be preferred to employ a third esterified alkoxylated polyol wherein at least one-third of the acyl groups present are $C_6$–$C_{19}$ unsaturated acyl groups. In a preferred embodiment, the third esterified alkoxylated polyol is comprised of a polyol residue derived from a polyhydric aliphatic compound which may be the same as or different from the polyol residue present in the first esterified alkoxylated polyol and from 2 to 8 fatty acid esterified oxyalkylene groups attached to said polyol residue, provided, of course, that at least one $C_6$–$C_{19}$ unsaturated acyl group is present. The fatty acid-esterified oxyalkylene groups preferably have the general structure

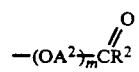

wherein $OA^2$ is an oxyalkylene unit derived from a $C_2$–$C_{10}$ epoxide which may be the same as or different from the oxyalkylene unit(s) in the first and second esterified alkoxylated polyols, m is from 1 to 20, and

is a $C_6$–$C_{24}$ acyl group, with the proviso that at least one acyl group is a $C_6$–$C_{19}$ unsaturated acyl group. Preferably, the $C_2$–$C_{10}$ epoxide is ethylene oxide, propylene oxide, 1,2-butylene oxide, or a mixture thereof. Suitable third esterified alkoxylated polyols may be prepared by any appropriate method, but the methods described hereinabove for preparation of the first esterified alkoxylated polyol are especially convenient, with the exception, of course, that the source of fatty acids will need to be selected so as to provide the desired level of $C_6$–$C_{19}$ unsaturated acyl groups. Other methods which are adoptable for this purpose are described in U.S. Pat. Nos. 4,861,613 and 4,983,329 and in copending application Ser. No. 07/227,048. The third esterified alkoxylated polyol should contain essentially no $C_{22}$ mono-unsaturated acyl groups derived from erucic acid in order to avoid any potential health risks upon consumption of the reduced calorie fat mimetic product.

To minimize the costs associated with the practice of this invention, it will be particularly appropriate to utilize a fatty acid mixture in the preparation of the third esterified alkoxylated polyol directly obtainable by hydrolytic splitting of a natural triglyceride relatively rich in $C_6$–$C_{19}$ unsaturated fatty acids. Such natural triglycerides are well-known and readily available and include, for example, corn oil (ca. 43 wt. % oleic acid and 39 wt. % linoleic acid), cottonseed oil (ca. 19 wt. % oleic acid and 50 wt. % linoleic acid), olive oil (ca. 64.5–84.5 wt. % oleic acid and 4–15 wt. % linoleic acid), palm oil (ca. 38–53 wt. % oleic acid and 6–12 wt. % linoleic acid), peanut oil (ca. 42.3–61 wt. % oleic acid and 13–33.5 wt. % linoleic acid), low erucic rapeseed (canola) oil (ca. 55–63 wt. % oleic acid and 20–31 wt. % linoleic acid), safflower oil (ca. 9.7–13.1 wt. % oleic acid and 76.9–80.5 wt. % linoleic acid), sesame oil (ca. 35–46 wt. % oleic acid and 35–48 wt. % linoleic acid), soybean oil (ca. 23.5–30.8 wt. % oleic acid, 49–51 wt. % linoleic acid, and 2–10.5 % linolenic acid), sunflower oil (ca. 14–43 wt. % oleic acid and 44–68 wt. % linoleic acid), lard (ca. 1.3–3.6 wt. % palmitoleic acid, 38.3–44.4 wt. % oleic acid, and 4.5–8.8 wt. % linoleic acid), beef tallow (ca. 26–50 wt. % oleic acid and 1–2.5 wt. % linoleic acid), as well as partially hydrogenated derivatives thereof. Mixtures of fatty acids from different triglyceride sources can also be used.

The relative amounts of the second and third esterified alkoxylated polyols used in the process of this invention are not critical. However, it will typically be desirable to transfer a sufficient number of $C_{20}$–$C_{24}$ saturated linear acyl groups from the second esterified alkoxylated polyol to the third esterified alkoxylated polyol such that the latter component's tendency to provoke undesired gastrointestinal side effects is minimized and its melting profile is shifted upwards to an appropriate extent. The amount of the second esterified alkoxylated polyol required for these purposes will be a function of its initial content of $C_{20}$–$C_{24}$ saturated linear acyl groups. At the same time, it will often be desirable to transfer sufficient $C_6$–$C_{19}$ unsaturated acyl groups from the third esterified alkoxylated polyol to the second esterified alkoxylated polyol that beneficial effects such as improved mouth feel or improved oxidative and/or thermal stabilities are realized. Thus, if there is a need to incorporate only a minor quantity of $C_6$-$C_{19}$ unsaturated acyl groups in the second esterified alkoxylated polyol composition, the amount of third esterified alkoxylated polyol composition utilized will be relatively small, especially if it is relatively rich in unsaturated acyl groups. Generally speaking, the weight ratio of second esterified alkoxylated polyol to third esterified alkoxylated polyol may be varied from at least 20:1 to 1:20.

The catalysts appropriate for use in the acyl group interchange step of the process will be those substances capable of catalyzing the desired transfer of acyl groups between the different starting components.

Such catalysts are typically basic in character and are preferably chosen from among those materials which are alkali metals, or alkali metal, alkaline earth, or ammonium compounds or tertiary amines since such substances exhibit high activity, tend to cause few problems with the formation of undesired by-products or impurities, may be readily removed by conventional techniques after the desired degree of acyl group interchange is accomplished, and do not generally raise any unusual concerns with respect to toxicity or other harmful effects if minor amounts remain in the reduced calorie fat mimetic product. Illustrative alkali metal, alkaline earth, or ammonium compounds which can be utilized include, but are not limited to ammonium, sodium, lithium, potassium, calcium, barium, or magnesium hydroxides, alkoxides (e.g., methoxides, ethoxides, salts of glycerin or other polyols such as diols, triols, tetrols, alkoxylated glycerin, and other polyhydric substances), carbonates, bicarbonates, hydrides, oxides, amides, carboxylates, phosphates, borates, sulfates, and the like. Metals such as sodium metal, potassium metal or a sodium-potassium alloy may also be employed. Suitable tertiary amines include, for example, pyridine, triethylamine, N,N-dimethylaniline, N-ethyl morpholine and the like. The amount of catalyst is not critical and the optimum concentration can be readily determined by routine experimentation. If the catalyst is an alkali metal or alkali metal, alkaline earth, or ammonium compound, typically the concentration of alkali metal, or alkaline earth, or nitrogen can suitably be in the range of from 50 to 10,000 parts per million based on the total combined weight of the second and third esterified alkoxylated polyols. When tertiary amines are utilized, catalyst concentrations of from 0.2 to 10 weight percent are generally appropriate.

In one embodiment of this invention, the basic catalyst which is required to accomplish acyl group interchange between the second and third esterified alkoxylated polyol is present in the third esterified alkoxylated polyol as a result of the production of the third esterified alkoxylated polyol itself. That is, the same basic alkali metal, alkali metal compound, alkaline earth compound, or tertiary amine may be utilized to catalyze the alkoxylation reaction of a polyol with an epoxide to form an alkoxylated polyol intermediate and the esterification reaction of the alkoxylated polyol intermediate with a fatty acid or fatty acid ester of a $C_1$-$C_6$ alcohol to produce the third esterified alkoxylated polyol as well as the acyl group interchange reaction of the second and third esterified alkoxylated polyols. The originally-charged basic catalyst is thus not removed prior to purification of the final desired reduced calorie fat mimetic composition. This embodiment provides a convenient and economical process for the preparation of such compositions since tedious and costly catalyst removal steps as well as the total amount of basic catalyst required are minimized.

The second and third esterified alkoxylated polyols are contacted in the presence of the basic catalyst for a time and at a temperature effective to accomplish at least partial transfer of the $C_{20}$-$C_{24}$ acyl groups present in the former substance to the latter substance. At the same time, $C_6$-$C_{19}$ unsaturated acyl group(s) are transferred from the third esterified alkoxylated polyol to the second esterified alkoxylated polyol replacing $C_{20}$-$C_{24}$ saturated linear acyl group(s). The reaction conditions are selected such that the desired degree of acyl group interchange takes place within a practically short period of time (typically, from about 5 minutes to 12 hours). It has been found that the oxyalkylene units present in the esterified alkoxylated polyol components are not affected or degraded by operation of the process of this invention, thus ensuring that the final product will be suitable for use in food compositions and that minimal purification or additional processing will be required.

Reaction temperatures of from 0° C. to 275° C. (more preferably, 50° C. to 200° C.) are normally suitable, although higher or lower temperatures could be utilized depending upon the activity of the catalyst. Although a solvent could be present in order to facilitate mixing, reduce viscosity, or aid in heat transfer, an important advantage of the process of this invention is that the use of a solvent is not required since both the second and third esterified alkoxylated polyols are typically relatively free-flowing liquids at the reaction temperatures normally employed. The components of the reaction mixture are preferably stirred, mixed, or agitated in a suitable reaction vessel in order to assure intimate contact on a molecular level and to facilitate the desired acyl group transfer reaction. The process of the invention is advantageously carried out under an inert atmosphere wherein air and oxygen are excluded in order to avoid oxidation of the reaction product. Unlike a conventional transesterification reaction of an alkoxylated polyol with $C_1$-$C_4$ alkyl esters of fatty acids or direct esterification with free fatty acids, no by-products (e.g., alcohol or water) need be removed from the reaction vessel during operation of the present process.

The reaction may be permitted to proceed until an equilibrium is attained wherein the different acyl groups are randomly distributed with respect to the different positions available for acyl group substitution in the initial esterified alkoxylated polyol components. This will maximize the $C_{20}$-$C_{24}$ saturated linear acyl group content of the third esterified alkoxylated polyol and the $C_6$-$C_{19}$ unsaturated acyl group content of the second esterified alkoxylated polyol. Alternatively, of course, the reaction may be halted at any point prior to reaching equilibrium by removing or deactivating the basic catalyst and/or cooling the mixture below the temperature at which acyl group interchange proceeds at a discernible rate. Another desirable benefit is that the equilibrium reaction product will be a reduced calorie lipid which is more homogeneous in character than the initial mixture of esterified alkoxylated polyols. That is, the second esterified alkoxylated polyol will tend to be a relatively high melting material which has a high solid fat index at or near room temperature owing to the high proportion of $C_{20}$-$C_{24}$ saturated acyl groups, while the third esterified alkoxylated polyol will tend to be a material which is completely or nearly completely liquid at room temperature, due to its high content of short chain unsaturated acyl groups. A simple mixture of these substances prior to acyl group interchange thus may be a heterogeneous blend at room temperature wherein solid particles of the second esterified alkoxylated polyol are dispersed in a matrix of liquid third esterified alkoxylated polyol. A blend having these characteristics may not be acceptable in all food applications. Once the acyl group interchange is carried out to equilibrium, however, the resulting reduced calorie fat mimetic composition will tend to be more uniform in appearance and exhibit a narrower melting range.

When the acyl group transfer reaction has proceeded to the extent desired, the basic catalyst may be removed or deactivated by any appropriate method. For example, if the basic catalyst is an alkali metal or an alkali metal, alkaline earth, or ammonium compound, the reaction product can be contacted with a particulate absorbent such as magnesium or aluminum silicate at an appropriate temperature (typically, 50° C. to 150° C.) so as to absorb the catalyst onto the absorbent and then filtered. Alternatively, the reaction product can be treated with an acid such as a mineral acid (e.g., hydrochloric acid, sulfuric acid, phosphoric acid) or an organic acid (e.g., acetic acid, oxalic acid, citric acid, tartaric acid) so as to neutralize the basic catalyst. The neutralized catalyst typically forms a precipitate which can be removed by filtration. Treatment with an appropriate ion exchange resin or extraction with water or dilute aqueous acid may also be utilized. Where the basic catalyst is a tertiary amine or other relatively volatile substance, it can be removed by distillation or steam stripping (preferably, under vacuum).

The reduced calorie fat mimetic produced by the process of this invention can be additionally purified or treated so as to render it more suitable for use in food compositions using any of the techniques known in the art for refining natural vegetable or animal oils and fats. Such techniques include, but are not limited to, degumming, bleaching, filtration, deodorization, hydrogenation, deacidification, steam stripping, dewaxing, and the like. Various additives such as stabilizers, anti-oxidants, vitamins and so forth can also be incorporated into the reduced calorie lipid.

Reduced calorie fat mimetic compositions produced in accordance with this invention can replace, in full or in part, conventional edible oils or fats in a cooking oil, frying oil, salad oil, or shortening, for example. Additional uses include combining the reduced calorie lipid with other foodstuff ingredients to form foods such as frozen desserts (e.g., sherbert, ice cream, frozen yogurt, milk shakes), baked goods (cakes, doughnuts, muffins, brownies, breads, pies, rolls, pastries, cookies, biscuits, crackers), nut butters (peanut butter), dairy products (margarine, sour cream, coffee lighteners, cheese, cheese spreads, flavored dips, filled cream, filled milk), mayonnaise, salad dressing, savory snacks (potato chips, corn chips, cheese puffs, pretzels, fried foods (fried poultry, fritters, fried pies, fried vegetables such as french fried potatoes, fried fish), reformed and comminuted meats (lunch meats, sausage, hot dogs, hamburger), pet foods, meat and egg substitutes or extenders, whipped toppings, gravies and other sauces, frostings, fillings, icings, cocoa butter replacements or blends, candies (especially those normally containing fatty ingredients such as chocolate or peanut butter), soups and dry baking mixes (for muffins, cakes, pancakes, waffles, brownies, and the like). Owing to the fat-like properties and stability of the reduced calorie fat mimetic compositions, minimum reformulation of standard foods will generally be required. The viscosity, melting profile, yield point, hardness, thixotropic area/liquid/solid stability, solid fat index, and other physical properties of the reduced calorie fat mimetic composition are preferably selected by manipulation of the chemical structures of the individual starting materials of the process such that the products mimic as closely as possible the analogous properties of the conventional triglyceride being replaced.

Illustrative ingredients which may be used in combination with the reduced calorie fat mimetic compositions obtainable by practice of this invention include carbohydrates (flour, starches, sugars, celluloses, polydextrose), edible lipids (triglycerides), proteins (from animal or vegetable sources), vitamins, antioxidants, emulsifiers, thickeners, preservatives, colorants, flavors, fragrances, sugar substitutes (saccharin, aspartame, sucralose, cyclamates, and the like), other fat substitutes or fat mimetics (for example, sucrose polyester or caprenin), water, milk, spices, eggs, and the like. Oil-in-water to water-in-oil emulsions can be readily prepared by combining water, the reduced calorie fat mimetic, and other ingredients such as emulsifiers. The reduced calorie fat mimetic s of this invention are particularly suitable for the preparation of food s requiring exposure to elevated temperatures. Unlike other proposed fat substitutes such as proteinacious macrocolloids or certain polysaccharide-based substances requiring water to render them fat-like in texture, the fat mimetic compositions produced by this invention are exceptionally stable thermally and do not readily decompose or lose their fat-like properties when heated. The compositions thus may readily be utilized in deep fat frying applications to prepare fried foods such as savory snacks, fried chicken, fried fish, french fries, and the like since they will function as effective heat transfer media (that is, they will transmit heat rapidly and uniformly to the food being fried and also provide crisping).

From the foregoing description, one skilled in the art can readily ascertain the essential characteristics of this invention and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

A first esterified propoxylated glycerin containing a high proportion of $C_{22}$ monounsaturated linear acyl groups is prepared by combining 382 parts by weight of a propoxylated glycerin obtained by reacting glycerin with 5 moles of propylene oxide per mole of glycerin in the presence of a potassium catalyst with 1100 parts by weight of a mixture of fatty acids obtained by hydrolytic splitting of a high erucic rapeseed oil and heating to 250° C. under a reduced pressure nitrogen atmosphere. When conversion of the hydroxyl groups in the initial propoxylated glycerin reaches 95%, the esterification is stopped and the product steam refined at 1 mm pressure and 5% steam per hour to an acid value of less than 0.3%.

The first esterified propoxylated glycerin thus obtained is then mixed with 0.2 weight percent Raney nickel hydrogenation catalyst and heated to 180° C.

under 50 psig hydrogen pressure. When the iodine value is less than 1, the second esterified propoxylated glycerin is cooled to 60° C. and filtered. After a second deodorization to remove a small amount of residual fatty acid, analysis of the product confirms that ca. 45 weight percent of the acyl groups have the structure

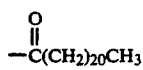

and less than 0.1 weight percent of the acyl groups are $C_{24}$ monounsaturated acyl groups.

The second esterified propoxylated glycerin (880 parts) is combined with a third esterified propoxylated glycerin (100 parts) and sodium methoxide (3 parts) and heated 3 hours at 150° C. The reduced calorie lipid composition thus obtained is filtered to remove most of the basic catalyst and then heated 1 hour at 110° C. with magnesium silicate (20 parts) and filtered again to remove residual sodium.

EXAMPLES 2-11

These examples illustrate alternative embodiments of the process of this invention wherein a variety of first and third esterified alkoxylated polyols having differing chemical compositions are utilized as shown in Table I. In each example, hydrogenation of the first esterified alkoxylated polyol is carried out for the time indicated or, in any event, for a time necessary to reduce the incidence of acyl groups having an erucic acid structure to less than 1 mole percent. Additionally, the first and third esterified alkoxylated polyols are prepared using a 10–20% molar excess (relative to the equivalents of hydroxyl present in the alkoxylated polyol intermediate) under conditions effective to achieve at least 95% conversion of the hydroxyl groups, with the excess fatty acids being removed by vacuum steam stripping.

TABLE 1

| Example No. | First Esterified Alkoxylated Polyol | | | | | Hydrogenation | | | | |
|---|---|---|---|---|---|---|---|---|---|---|
| | Polyol | Epoxide | Moles Epoxide/ Mole Polyol | pbw[1] | Fatty Acid Source | Catalyst | pbw | Time hr. | Temp., °C. | $H_2$ Pressure atm |
| 2 | 2,3-butane-diol | ethylene oxide | 10 | 100 | a | nickel on Kieselguhr (60% Ni) | 1 | 4 | 160 | 1 |
| 3 | trimethylol propane | 1,2-butylene oxide | 15 | 100 | b | double Ni Al salt[5] | 1 | 4 | 160 | 1 |
| 4 | sorbitol | EO/PO[2] | 12 | 100 | c | Cu Ni on silica[6] | 1.4 | 6 | 200 | 5 |
| 5 | sucrose | PO/EO[3] | 20 | 100 | d | copper chromate[7] | 2 | 8 | 175 | 3.5 |
| 6 | methyl glucoside | PO/BO[4] | 4 | 100 | e | 5% Pd on carbon | 0.2 | 3 | 175 | 3 |
| 7 | 1,2,6-tri-hydroxyhexane | methyl glycidyl ether | 8 | 100 | a | wet reduced nickel[9] | 1 | 5 | 180 | 2 |
| 8 | penta-erythritol | 1,2-octene oxide | 24 | 100 | b | 1% Pt on alumina | 1 | 6 | 150 | 2 |
| 9 | propylene glycol | phenyl glycidyl ether | 6 | 100 | c | nickel on silica/alumina (64% Ni) | 0.75 | 10 | 200 | 1.5 |
| 10 | 1,2-cyclo hexanediol | 1,2 pentene oxide | 10 | 100 | d | Ni Ag on Kieselguhr[10] | 1.5 | 12 | 140 | 4 |
| 11 | 2,3,4-trihydroxy pentane | propylene oxide | 9 | 100 | e | Raney nickel | 1 | 5 | 200 | 6 |

| Example No. | Third Esterified Alkoxylated Polyol | | | | | Acyl Group Interchange Conditions | | | |
|---|---|---|---|---|---|---|---|---|---|
| | Polyol | Epoxide | Moles Epoxide/ Mole Polyol | pbw[1] | Fatty Acid Source | Basic Catalyst | pbw | Time hr. | Temp., °C. |
| 2 | 2,3-butane diol | ethylene oxide | 10 | 10 | f | potassium methoxide | 0.4 | 1.5 | 175 |
| 3 | trimethylol propane | 1,2-butylene oxide | 15 | 15 | g | sodium hydroxide | 1 | 0.5 | 225 |
| 4 | sorbitol | EO/PO[2] | 12 | 20 | h | sodium stearate | 0.75 | 1.0 | 250 |
| 5 | sucrose | PO/EO[3] | 20 | 25 | i | sodium dispersion (in xylene) | 0.5 | 2.0 | 95 |
| 6 | methyl glycoside | PO/BO[4] | 4 | 5 | j | potassium hydroxide | 2 | 4.0 | 200 |
| 7 | glycerin | propylene oxide | 20 | 30 | k | sodium | 0.7 | 0.5 | 100 |
| 8 | 1,4-butane diol | propylene oxide | 10 | 15 | l | potassium hydride | 1.0 | 0.25 | 170 |
| 9 | 1,2,4-butanetriol | propylene oxide | 15 | 10 | m | calcium oxide | 3.0 | 5.0 | 200 |
| 10 | penta-erythritol | propylene oxide | 16 | 10 | n | sodium amide (in toluene) | 1.0 | 4.0 | 60 |
| 11 | xylitol | propylene oxide | 30 | 20 | o | Na—K alloy | 0.5 | 0.5 | 100 |

TABLE 1-continued

50/50 wt/wt

FOOTNOTES
a. mixture of fatty acids obtained by hydrolytic splitting of meadow foam oil (ca. 62.6% 20:1 Δ5, 2.6% 22:1 Δ5, 9.7% 22:1 Δ13, 22.1% 22:2 Δ5, 13)
b. mixture of fatty acids obtained by hydrolytic splitting of Polish rapeseed oil (ca. 2.8% palmitic acid, 1.2% stearic acid, 0.9% arachidic acid, 0.6% behenic acid, 0.7% lignoceric acid, 2.9% hexadecenoic acid, 14.2% oleic acid, 3.5% eicosenoic acid, 52.5% erucic acid, 12.0% linoleic acid, 1.1% docosadienic acid, 7.6% linolenic acid)
c. mixture of fatty acid obtained by hydrolytic splitting of ravison oil (ca. 4.3% palmitic acid, 2.1% stearic acid, 1.8% arachidic acid, 0.5% behenic acid, 0.0% lignoceric acid, 0.6% hexadecenoic acid, 15.5% oleic acid, 4.1% eicosenoic acid, 38.7% erucic acid, 20.9% linoleic acid, 1.0% docosadienic acid, 9.9% linolenic acid)
d. mixture of fatty acids obtained by hydrolytic splitting of mustard seed oil (ca. 1.5% palmitic acid, 0.4% stearic acid, 0.5% arachidic acid, 2.0% behenic acid, 1.0% lignoceric acid, 22.0% oleic acid, 7.0% eicosenoic acid, 44.2% erucic acid, 14.2% linoleic acid, 6.8% linolenic acid)
e. mixture of fatty acids obtained by hydrolytic splitting of Crambe abyssinica oil (ca. 2.0 wt. % 16:0, 0.4 wt. % 16:1, 0.1 wt. % 16:3, 0.4 wt. % 18:0, 16.9 wt. % 18:1, 8.6 wt. % 18:2, 6.4 wt. % 18:3, 0.5 wt. % 20:0, 3.2 wt. % 20:1, 0.2 wt. % 20:2, 2.0 wt. % 22:0, 57.2 wt. % 22:1, 0.8 wt. % 22:2, 1.4 wt. % 24:1)
f. mixture of fatty acids obtained by hydrolytic splitting of palm kernel oil (ca. 0.2 wt. % caproic acid, 4.8 wt. % caprylic acid, 6.6 wt. % caprice acid, 44.1 wt. % lauric acid, 15.4 wt. % myristic acid, 8.5 wt. % palmitic acid, 2.7 wt. % stearic acid, 0.2 wt. % arachidic acid, 16.1 wt. % oleic acid, 1.4 wt. % linoleic acid)
g. mixture of fatty acids obtained by hydrolytic splitting of cocoa butter (ca. 24.4 wt. % palmitic acid, 35.4 wt. % stearic acid, 38.1 wt. % oleic acid, 2.1 wt. % linoleic acid)
h. mixture of fatty acids obtained by hydrolytic splitting of lard (ca. 1.3 wt. % myristic acid, 28.3 wt. % palmitic acid, 11.9 wt. % stearic acid, 0.2 wt. % tetradecenoic acid, 2.7 wt. % hexadecenoic acid, 47.5 wt. % oleic acid, 6.0 wt. % linoleic acid, 2.1 wt. % $C_{20}$ + $C_{22}$ unsaturated fatty acids)
i. mixture of fatty acids obtained by hydrolytic splitting of beef tallow (ca. 6.3 wt. % myristic acid, 27.4 wt. % palmitic acid, 14.1 wt. % stearic acid, 49.6 wt. % oleic acid, 2.5 wt. % octadecenoic acid)
j. mixture of fatty acids obtained by hydrolytic splitting of cottonseed oil (ca. 1.4 wt. % myristic acid, 23.4 wt. % palmitic acid, 1.1 wt. % stearic acid, 1.3 wt. % arachidic acid, 0.1 wt. % tetradecenoic acid, 2.0 wt. % hexadecenoic acid, 22.9 wt. % oleic acid, 47.8 wt. % linoleic acid)
k. mixture of fatty acids obtained by hydrolytic splitting of peanut oil (ca. 0.5 wt. % myristic acid, 8.0 wt. % palmitic acid, 4.4 wt. % stearic acid, 2.4 wt. % arachidic acid, 3.1 wt. % behenic acid, 1.1 wt. % lignoceric acid, 1.7 wt. % hexadecenoic acid, 52.5 wt. % oleic acid, 26.3 wt. % linoleic acid)
l. mixture of fatty acids obtained by hydrolytic splitting of palm oil (ca. 1.6 wt. % myristic acid, 32.3 wt. % plamitic acid, 5.5 wt. % stearic acid, 52.4 wt. % oleic acid, 8.2 wt. % linoleic acid)
m. mixture of fatty acids obtained by hydrolytic splitting of sunflower oil (ca. 3.6 wt. % palmitic acid, 2.9 wt. % stearic acid, 0.6 wt. % arachidic acid, 0.4 wt. % lignoceric acid, 34.0 wt. % oleic acid, 57.5 wt. % linoleic acid)
n. mixture of fatty acids obtained by hydrolytic splitting of corn oil (ca. 13 wt. % palmitic acid, 4 wt. % stearic acid, 29. wt. % oleic acid, 54 wt. % linoleic acid)
o. mixture of fatty acids obtained by hydrolytic splitting of safflower oil (ca. 6.4 wt. % palmitic acid, 3.1 wt. % stearic acid, 0.2 wt. % arachidic acid, 13.4 wt. % oleic acid, 76.9 wt. % linoleic acid)
[1] parts by weight
[2] EO = ethylene oxide, PO = propylene oxide; 6 moles EO per mole sorbitol reacted first, followed by 6 moles PO per mole sorbitol
[3] 5 moles and 15 moles per mole sucrose reacted as a mixture.
[4] PO = propylene oxide; BO = 1,2-butene oxide; 2 moles of PO and 2 moles of BO per mole methyl glucoside reacted as a mixture
[5] Example 1, U.S. Pat. No. 3,896,053 (Broecker et al.)
[6] Example 1, U.S. Pat. No. 3,743,662 (Eurlings et al.)
[7] Lazier et al., Org. Syn. Coll. 2, 142 (1943)
[8] Mozingo, Org. Syn. Coll. 3, 685 (1955)
[9] 25% metallic nickel, 75% hardened vegetable oil
[10] LeFebrure et al., Fette, Seifen, Anstrichm. 77, 125 (1975)

EXAMPLE 12

Propoxylated glycerin containing 5 moles of propylene oxide per mole of glycerin (382 parts by weight) is mixed with non-hydrogenated high erucic rapeseed fatty acids (1100 parts) in a reaction vessel and heated to 250° C. under a reduced pressure nitrogen atmosphere until hydroxyl group conversion is 95%. The resulting mixture of esterified propoxylated glycerin and excess fatty acid is then fed through a continuous deodorizer at 1–3 mm pressure using 5% steam per hour to remove the excess fatty acid. As little or no $C_{20}$–$C_{24}$ saturated fatty acids are present, no problems with plugging are encountered. The acid value of the deodorized esterified propoxylated glycerin is 0.3% or less.

The esterified propoxylated glycerin containing acyl groups derived from the non-hydrogenated high erucic rapeseed fatty acids is then placed in a stirred hydrogenation vessel and a nickel hydrogenation catalyst is added to a concentration of 0.2 weight % Ni. The reactor is sealed and heated to 180° C. under 50 psig hydrogen pressure. Hydrogen is introduced during the course of the hydrogenation to maintain a constant pressure. When the iodine value of the reaction mixture is less than 1, the product is cooled to 60° C., filtered through a pressurized plate filter, and returned continuously to the reactor until the filtrate is free of nickel catalyst. The product is redeodorized under the conditions described above. A different esterified propoxylated glycerin (142 parts) prepared as described above with the exception that a mixture of fatty acids obtained by hydrolytic splitting of soybean oil is utilized in place of the non-hydrogenated rapeseed fatty acids, is then added to the reactor, followed by sufficient sodium methoxide to provide a sodium concentration of 0.2 weight %. The temperature is increased to 150° C. for 3 hours to accomplish acyl group interchange. After treatment with magnesium silicate and filtration to remove the residual sodium catalyst, the reduced calorie fat mimetic composition is redeodorized to yield a final product which is indistinguishable from a product prepared from 382 molecular weight propoxylated glycerin and a 9:1 (w/w) mixture of hydrogenated rapeseed fatty acids and soybean fatty acids, yet which did not require the use of long chain saturated fatty acids in its preparation.

EXAMPLE 13

Propoxylated glycerin containing 5 moles of propylene oxide per mole of glycerin (382 parts by weight) is mixed with non-hydrogenated high erucic rapeseed fatty acids (1100 parts) in a batch deodorizer and heated to 250° C. under a reduced pressure nitrogen atmosphere. No steam is introduced into the deodorizer during this step. Samples are taken hourly until the hydroxyl group conversion reaches 95%. Steam is then introduced at 1–3 mm pressure and 10% steam per hour to deodorize the esterified propoxylated glycerin and to remove the unreacted excess fatty acid; vacuum steam stripping is halted once the acid value is 0.3% or less.

The esterified propoxylated glycerin thus obtained is hydrogenated and then reacted with a second esterified propoxylated glycerin derived from soybean fatty acids in the same manner as described in Example 12. The reduced calorie fat mimetic composition produced is expected to be identical to the product of Example 12.

I claim:

1. A process for producing a reduced calorie fat mimetic comprising the steps of
   (a) contacting a first esterified alkoxylated polyol characterized by the presence of at least one $C_{20}$–$C_{24}$ unsaturated linear acyl group with hydrogen in the presence of a transition metal catalyst for a time and at a temperature effective to accomplish hydrogenation of the $C_{20}$–$C_{24}$ unsaturated linear acyl group to yield a second esterified alkoxylated polyol characterized by the presence of at least one $C_{20}$–$C_{24}$ saturated linear acyl group and the absence of any $C_{22}$ unsaturated linear acyl group; and (b) contacting the second esterified alkoxylated polyol with a third esterified alkoxylated polyol characterized by the presence of at least one $C_6$–$C_{19}$ unsaturated acyl group in the presence of a basic catalyst for a time and at a temperature effective to accomplish interchange of at least one $C_{20}$–$C_{24}$ saturated linear acyl group and at least one $C_6$–$C_{19}$ unsaturated acyl group to yield the reduced calorie fat mimetic.

2. The process of claim 1 wherein the first esterified alkoxylated polyol is comprised of a polyol residue derived from a polyhydric aliphatic compound and from 2 to 8 fatty acid-esterified oxyalkylene groups connected to said polyol residue.

3. The process of claim 2 wherein at least one of the fatty acid-esterified oxyalkylene groups has the general structure

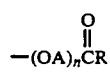

wherein OA is an oxyalkylene unit derived from a $C_2$–$C_{10}$ epoxide, n is from 1 to 20, and

is an acyl group derived from a $C_{20}$–$C_{24}$ unsaturated fatty acid.

4. The process of claim 3 wherein the $C_{20}$–$C_{24}$ unsaturated linear fatty acid is selected from eicosenoic acids, docosenoic acids, and docosadienoic acids.

5. The process of claim 2 wherein at least one-half of the fatty acid-esterified oxyalkylene groups have the general structure

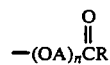

wherein OA is an oxyalkylene unit derived from a $C_2$–$C_{10}$ epoxide, n is from 1 to 20, and

is an acyl group derived from a $C_{20}$–$C_{24}$ unsaturated fatty acid.

6. The process of claim 2 wherein the polyhydric aliphatic compound is selected from the group consisting of $C_2$–$C_{10}$ aliphatic diols, $C_3$–$C_{12}$ aliphatic triols, pentaerythritol, sugar alcohols, monosaccharides, disaccharides, and alkyl glycosides.

7. The process of claim 1 wherein step (a) is carried out at a hydrogen pressure of from 0.5 to 20 atmospheres.

8. The process of claim 1 wherein the transition metal catalyst is selected from the group consisting of nickel- and copper-containing catalysts.

9. The process of claim 1 wherein the temperature in step (a) is from 75° to 275° C.

10. The process of claim 1 wherein the time in step (a) is from 0.5 to 24 hours.

11. The process of claim 1 wherein the basic catalyst is selected from the group consisting of tertiary amines, alkali metals, alkali metal compounds, alkaline earth compounds, and ammonium compounds.

12. The process of claim 1 wherein the third esterified alkoxylated polyol is comprised of a polyol residue derived from a polyhydric aliphatic compound and from 2 to 8 fatty acid-esterified oxyalkylene groups connected to said polyol residue.

13. The process of claim 12 wherein at least one of the fatty acid-esterified oxyalkylene groups has the general structure

wherein OA is an oxyalkylene unit derived from a $C_2$–$C_{10}$ epoxide, n is from 1 to 20, and

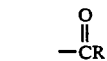

is an acyl group derived from a $C_6$–$C_{19}$ unsaturated fatty acid.

14. The process of claim 13 wherein OA has the general structure

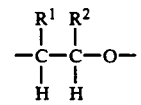

wherein $R^1$ and $R^2$ are the same or different and are selected from the group consisting of hydrogen, methyl, and ethyl.

15. The process of claim 12 wherein at least one-third of the fatty acid-esterified oxyalkylene groups have the general structure

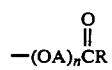

wherein OA is an oxyalkylene unit derived from a $C_2$–$C_{10}$ epoxide, n is from 1 to 20, and

is an acyl group derived from a $C_6$–$C_{19}$ unsaturated fatty acid.

16. The process of claim 1 wherein the third esterified alkoxylated polyol is characterized by the absence of $C_{22}$ unsaturated acyl groups.

17. The process of claim 1 wherein step (b) is carried out at a temperature of from 0° C. to 275° C.

18. A process for producing a reduced calorie fat mimetic composition comprising the steps of (a) contacting a first esterified alkoxylated polyol comprised of (i) a first polyol residue derived from a first polyhydric aliphatic compound and (ii) 2 to 8 fatty acid-esterified oxyalkylene groups connected to said first polyol residue wherein at least one-half of the fatty acid-esterified oxyalkylene groups have the general structure

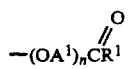

wherein $OA^1$ is a first oxyalkylene unit derived from a first $C_2$–$C_{10}$ aliphatic epoxide, n is from 1 to 20, and

is an acyl group derived from a $C_{20}$–$C_{24}$ unsaturated linear fatty acid with hydrogen in the presence of a catalyst containing nickel or copper at a pressure of from 0.5 to 20 atmospheres and a temperature of from 75° C. to 275° C. for a time effective to accomplish hydrogenation of the acyl group derived from the $C_{20}$–$C_{24}$ unsaturated linear fatty acid to yield a second esterified alkoxylated polyol characterized by the presence of at least one $C_{20}$–$C_{24}$ saturated linear acyl group and the absence of any $C_{22}$ unsaturated linear acyl groups; and b) contacting the second esterified alkoxylated polyol with a third esterified alkoxylated polyol comprised of (i) a second polyol residue which is the same as or different from the first polyol residue derived from a second polyhydric aliphatic compound which is the same as or different from the first polyhydric aliphatic compound and (ii) from 2 to 8 fatty acid-esterified oxyalkylene groups connected to said second polyol residue wherein at least one of the fatty acid-esterified oxyalkylene groups has the general structure

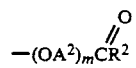

wherein $OA^2$ is a second oxyalkylene unit derived from a second $C_2$–$C_{10}$ aliphatic epoxide which may be the same as or different from the first $C_2$–$C_{10}$ aliphatic epoxide, m is from 1 to 20, and

is an acyl group derived from a $C_6$–$C_{19}$ unsaturated fatty acid in the presence of an alkali metal or alkali metal compound at a temperature of from 0° C. to 275° C. for a time effective to accomplish interchange of at least one $C_{20}$–$C_{24}$ saturated linear acyl group in the second esterified alkoxylated polyol and at least one acyl group derived from a $C_6$–$C_{19}$ unsaturated fatty acid in the third esterified alkoxylated polyol to yield the reduced calorie fat mimetic composition.

19. The process of claim 18 wherein the first and second polyhydric aliphatic compounds are both glycerin.

20. The process of claim 18 wherein the first and second $C_2$–$C_{10}$ aliphatic epoxides are both selected from the group consisting of ethylene oxide, propylene oxide, 1,2-butylene oxide, and mixtures thereof.

* * * * *